United States Patent [19]

Farr, deceased

[11] Patent Number: 4,566,452
[45] Date of Patent: Jan. 28, 1986

[54] NEBULIZER

[75] Inventor: James I. Farr, deceased, late of Upland, Calif., by May S. Farr, administrator

[73] Assignee: American Hospital Supply Corporation, Evanston, Ill.

[21] Appl. No.: 641,927

[22] Filed: Aug. 17, 1984

Related U.S. Application Data

[63] Continuation of Ser. No. 397,669, Jul. 12, 1982, abandoned.

[51] Int. Cl.$^4$ ............................................. A61M 16/00
[52] U.S. Cl. .......................... 128/200.21; 128/200.18; 239/338
[58] Field of Search ...................... 128/200.14, 200.18, 128/204.16, 200.21, 200.16; 261/DIG. 48, DIG. 65, DIG. 78; 239/338, 366, 367, 368, 369, 370, 386, 388, 424

[56] References Cited

U.S. PATENT DOCUMENTS

| | | | |
|---|---|---|---|
| 2,709,577 | 5/1955 | Pohndorf et al. | 128/200.21 |
| 2,726,896 | 12/1955 | McKinnon | 239/338 |
| 2,993,652 | 7/1961 | Curry | 239/338 |
| 3,069,097 | 12/1962 | Cheney | 239/338 |
| 3,172,406 | 3/1965 | Bird et al. | 128/200.21 |
| 3,744,722 | 7/1973 | Burns | 239/338 |
| 3,762,409 | 10/1973 | Lester | 128/200.14 |
| 3,999,713 | 12/1976 | Lindsey | 239/338 |
| 4,054,622 | 10/1977 | Lester | 128/200.18 |
| 4,263,907 | 4/1981 | Lindsey | 128/200.21 |
| 4,299,355 | 11/1981 | Hakkinen | 239/338 |
| 4,333,450 | 6/1982 | Lester | 128/200.14 |
| 4,512,341 | 4/1985 | Lester | 128/200.21 |

Primary Examiner—Henry J. Recla
Assistant Examiner—Karin M. Reichle
Attorney, Agent, or Firm—Roger A. Williams

[57] ABSTRACT

A nebulizer for converting liquid into aerosol which includes a housing having a sidewall defining a liquid reservoir and an outlet opening through which aerosol passes. A gas nozzle having a gas orifice is included in the nebulizer, which gas nozzle has a gas inlet for introducing gas to the nozzle. A liquid inlet is provided on the nebulizer which is spaced from the gas nozzle for introducing liquid to the gas nozzle as gas flows through the gas orifice. A liquid passage in communication with the reservoir and the liquid inlet is provided, which liquid passage extends along and spaced from the sidewall of the housing which defines the liquid reservoir.

14 Claims, 4 Drawing Figures

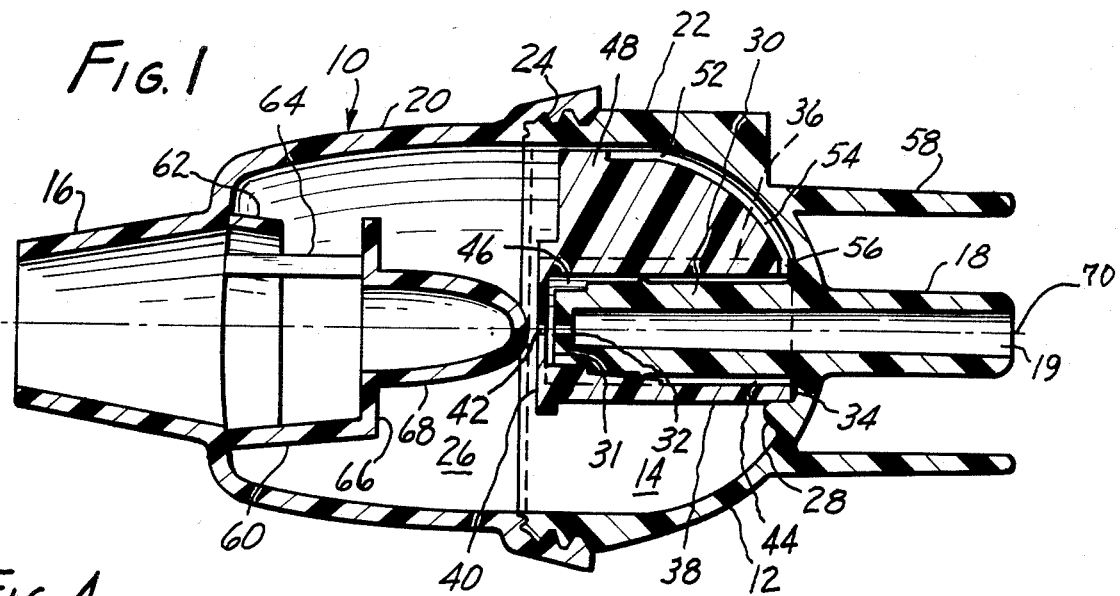

NEBULIZER

This application is a continuation of application Ser. No. 397,669, filed July 12, 1982, now abandoned.

BACKGROUND OF THE INVENTION

The invention herein is directed to a new and improved nebulizer for converting liquid into an aerosol. The nebulizer herein is particularly suited for medical applications, although may be useful in other applications wherein it is desirable to mix liquid with a gas.

Nebulizers are pneumatic devices which are designed to break up liquid medication into small particles and to entrain the small liquid particles in a stream of air or gas, which air or gas provides an aerosol for inhalation therapy in the treatment of respiratory system disorders. It is important during inhalation therapy that there be a sufficient quantity and proper formation of aerosol provided by the nebulizer. If the particles or droplets of the liquid medication are too fine, they are not likely to be retained in the respiratory track but will, to a great extent, be exhaled. If the particles are too large, they will likely be deposited on the upper reaches of the respiratory system, such as the trachea and the upper tracheal-bronchial tree, thereby leaving the rest of the system untreated. It is also important that the aerosol be delivered to the patient in a smooth, uniform manner.

A variety of nebulizers are commercially available. Many of such commercially available nebulizers are referred to as hand-held nebulizers. Such hand-held nebulizers are designed for being held by the patient receiving inhalation therapy treatment. The nebulizers can be for repeated use after sterilization or may be disposable. Generally, the disposable nebulizers are constructed of plastic. In many single use or individual patient hand-held nebulizers, the nebulizer is a relatively small design, generally about three inches long and designed to hold about 10 cc's of liquid medication or less.

A drawback with the commercially available nebulizers is that they do not utilize the entire volume of liquid medication. That is, as the volume of the medication decreases in the reservoir of the nebulizer below the volume necessary to maintain the syphon action, the syphon action stops, leaving an unnecessarily large amount of medication in the reservoir. In such operations, the attendant may add additional medication or will dispose of the nebulizer. When the nebulizer is removed from the inhalation circuit, some of the liquid medication remains in the nebulizer. Either the addition of additional medication or disposing of the nebulizer with liquid medication remaining in the bowl are undesirable and costly due to the expense of the liquid medication. It would be desirable to have a nebulizer which can substantially utilize all of the liquid medication in the nebulizer or at least a substantial volume of such liquid medication.

In addition to the above drawback, the hand-held nebulizers are sufficiently small that it is difficult to keep the nebulizers oriented in a particular direction. That is, during use the hand-held nebulizer may assume various positions such as lying on its side or being angled in a variety of different positions by the patient holding the nebulizer. For example, it is required in many nebulizers to maintain the nebulizer in an upright position with regard to a vertical axis extending through the outlet opening through which the aerosol passes. Many nebulizers are designed to operate efficiently, providing a beneficiating aerosol only when the nebulizer is maintained in a specific orientation with regard to the exhausted aerosol or possibly the gas or air spray. It would be desirable to have a nebulizer which could operate efficiently to provide a beneficial aerosol substantially independent of the orientation of the nebulizer, or easy to orientate by the patient in a variety of beneficial operating positions, and which would also utilize substantially all of the liquid medication in the nebulizer.

SUMMARY OF THE INVENTION

The invention herein is directed to a nebulizer for converting liquid into aerosol and, in particular, to a nebulizer which can utilize substantially all of the liquid medication placed in the nebulizer and which will provide a beneficial aerosol when the nebulizer is oriented in a variety of positions.

The nebulizer includes a housing having a sidewall which defines a liquid reservoir. An outlet opening is provided in the housing through which the aerosol can pass. A gas nozzle is provided within the housing for introducing gas which can mix with the liquid medication to entrain such liquid medication. A gas orifice is provided on the gas nozzle. A liquid inlet is provided on the nebulizer which is proximate to the gas orifice such that gas flowing through the gas orifice causes liquid to flow through the liquid inlet. That is, when gas passes through the gas orifice, liquid is drawn from the reservoir through the liquid inlet such that it can mix with the gas sprayed from the gas orifice. The nebulizer also includes a liquid passage which is in communication with the liquid inlet and reservoir. At least a portion of the liquid passage extends along and is spaced from the sidewall of the housing which defines the reservoir. That is, at least a portion of the liquid passage extends within the reservoir along and spaced from a portion of the sidewall.

BRIEF DESCRIPTION OF THE DRAWINGS

The objects and advantages of the nebulizer herein will be apparent from the following description and accompanying drawings wherein:

FIG. 1 is a side cross-sectional view illustrating the nebulizer;

FIG. 2 is an enlarged side cross-sectional view of the spray assembly for the nebulizer shown in FIG. 1;

FIG. 3 is a top elevational view of the spray assembly shown in FIG. 2; and

FIG. 4 is an enlarged top elevational view of the bowl component of the nebulizer shown in FIG. 1.

DETAILED DESCRIPTION

The nebulizer which is the subject of the invention herein will be described with regard to the accompanying drawings. With regard to FIG. 1, the nebulizer device 10 is illustrated. The nebulizer can be constructed of any suitable material, including plastic such as crystal polystyrene. The nebulizer is structured such that it includes only three separately molded components: a cap component 20; a bowl component 22; and a spray assembly 36. Each of these components can be quickly and easily injection molded and then assembled without the need for expensive additional machinery.

The nebulizer 10 has a sidewall 12 which forms a reservoir 14 for holding the liquid medication. An outlet 16 is provided on the nebulizer which defines an opening through which the aerosol can pass. The outlet 16 is designed so that suitable tubing can be adapted to provide a passageway for the aerosol to the patient as it leaves the nebulizer. A gas inlet 18 is provided to the nebulizer 10 as a conduit for the gas to be used in the nebulization of the liquid medication. The gas inlet 18 is constructed so that it can be fitted with suitable tubing which can be connected to the source for the gas.

As discussed above, the nebulizer is constructed of three separate components. The cap component 20 and the bowl component 22 can be joined together through suitable joining means such as the threaded connection illustrated in FIG. 1 by the threads 24 on both the cap and bowl components. The spray assembly 36 can be snap-fitted within the bowl component. When the three components of the nebulizer are assembled, the housing forms a reservoir 14 and a mixing chamber 26 above the liquid reservoir. The cap component and bowl component interlock, such as through the threads 24 to insure proper alignment of the bowl and cover components. Together the bowl component and the cover component form the housing having a generally smooth inner surface which defines the mixing area 26 in the upper portion and a reservoir 14 in the lower portion of the housing. The reservoir 14 is adapted to hold any suitable volume of liquid medication, but preferably is designed to hold about eight cubic centimeters of liquid medication. The mixing chamber 26 is of sufficient volume to minimize the attractive action of the sidewall and material of the housing for the droplets of medication which otherwise might interfere with the operation of the nebulizer.

The bowl component 22 will be described with regard to FIGS. 1 and 4. The bowl component is generally cup-shaped with a generally smooth wall 12 forming the reservoir 14. Centered within the reservoir and bowl component is a cylindrical gas nozzle 30. The gas nozzle 30 is an integrally molded element with the gas inlet 18. That is, the gas inlet passage 19 is a smooth wall inlet extending through the gas inlet 18, through the gas nozzle 30 and opening into the nebulizer through a gas orifice 32 defined by the end wall of the gas nozzle. The end portion of the gas nozzle 30 can have a lesser outer diameter that the main body portion of the gas nozzle as is shown in FIG. 1. Such a lesser outer diameter configuration provides an annular passage 44 and a mixing passage 46 lying between the respective end walls 31 and 40 of the gas nozzle and spray nozzle which will be described later herein.

Extending around and spaced from the gas nozzle is an annular ring 28. The annular ring 28 does not completely encircle the gas nozzle as a gap 50 is provided on the annular ring. The annular ring 28 extends upwardly, substantially parallel to the gas nozzle.

A spray assembly 36 is fitted within the bowl component 22. The spray assembly 36 will be described herein with regard to FIGS. 1, 2 and 3. The spray assembly 36 forms a spray nozzle 38 which defines and encircles an inner chamber 39. The spray assembly 36 snap fits over the gas nozzle 30. The chamber 39 of the spray assembly receives the gas nozzle. The gas nozzle can be slightly tapered, as well as the chamber 39, to provide a good fit. The chamber can be provided with spaced apart ribs 41 for retaining the spray assembly on the gas nozzle. Such ribs can help maintain the proper spacing between the gas nozzle and spray nozzle, including their respective orifices. The diameter of the chamber 39 is slightly greater than the outside diameter of the gas nozzle, thus forming an annular passage 44 extending between the gas and spray nozzles. The annular passage 44 is open along the entire length of the gas nozzle. The spray assembly has an outer diameter sufficient for fitting within the annulus 34 between the incomplete annular ring 28 and the gas nozzle 30.

The spray nozzle 38 has an end wall 40 which can be flat as shown, tapered or be provided with a recess. The spray nozzle end wall defines a spray orifice 42 which is axially aligned with the gas orifice 32.

As stated above, an annular passage 44 is open between the spray nozzle 38 and gas nozzle 30. A space is also provided between the gas nozzle end wall 31 and the spray nozzle end wall 40. The end walls of both the gas nozzle and spray nozzle being spaced apart form a mixing passage 46 wherein the gas and liquid medication can be mixed prior to passing through the spray orifice.

The spray assembly is provided with an extended side 48. The extended side 48 projects outwardly from the spray nozzle and is adapted to snugly fit through the gap 50 in the incomplete annular ring 28. The extended side extends outwardly toward the sidewall 12 of the bowl component. An upper portion of the extended side is in close proximity to the sidewall 12 of the bowl component. A liquid passage 52 is provided on the extended side. The liquid passage 52 extends along the extended side and extends along at least a portion of the sidewall 12 of the bowl component. The liquid passage is spaced from the sidewall 12 and open along its length to the reservoir. The liquid passage 52 can have any cross section and, as shown in FIG. 3, has a cross section in the preferred embodiment that is semicircular. The liquid passage 52 extends along the extended side and opens into the annular passage 44 lying between the gas nozzle and spray nozzle providing fluid-flow communication from the reservoir to the annular passage. The liquid passage 52 extends along the extended side and follows the contour of the sidewall 12 of the reservoir. In a preferred embodiment, the liquid passage 52 extends along the sidewall to a location which would be the lowest location in the housing if the housing were laid on its side. Preferably, the liquid passage extends along the sidewall from the spray nozzle to a location up to intersection of the plane of the spray nozzle with the sidewall. The plane of the spray nozzle is substantially perpendicular to an axis 70 extending through the spray and gas orifices.

The liquid passage 52 provides for pickup of the liquid medication within the reservoir. When the nebulizer is positioned in an upright position, the liquid medication can flow through the space 54 between the liquid passage 52 and sidewall 12. The liquid medication flows into the liquid passage and then along the liquid passage and into the annular passage 44. The liquid medication then flows along the annular passage 44 toward the mixing passage 46 wherein it mixes with the incoming gas. As the nebulizer is slanted toward the side to which the extended side extends, liquid medication can still be drawn through the liquid passage 52. If the nebulizer were placed in a horizontal position with the extended side extending downwardly, the liquid medication can still be drawn through the liquid passage 52 as it extends to what would be the lowest position in the reservoir when the nebulizer is on its side. The liquid medication would flow along the liquid passage 52 through a gap 56 through the sidewall of the spray nozzle and into the annular passage 44.

The liquid passage 52 extends along and is spaced from the sidewall 12 by a distance that is sufficient to permit liquid medication to flow into the liquid passageway, but which is small enough to maintain a liquid seal between the extended side and sidewall due to surface tension in the liquid medication when the nebulizer is positioned in an off axis (reference to axis 70) position. In a preferred embodiment, it has been found that the liquid passage can be spaced from about 0.0010 to about 0.025 inch from the sidewall and provide such characteristics when the liquid passage has a semicircular cross section with a 0.050 inch radius. In the most preferred embodiment, the liquid passage was spaced about 0.010 inch from the sidewall.

The bowl component can also be provided with integrally molded supports 58. These supports 58 can help position the nebulizer and can help support the nebulizer when it is not clamped to a stand and the gas supply tube is not attached. The supports 58 can maintain the nebulizer in an upright position once it is filled by the physician and prior to attaching the connecting gas supply hose, thus preventing tipping of the nebulizer which can cause loss of the liquid medication.

The cap component provides the cap or enclosing top to the nebulizer. The cap component encloses the mixing chamber 26 and provides the outlet 16 for the aerosol.

In a preferred embodiment, the cap component also includes a diffuser assembly 60. The diffuser assembly provides a diffuser or baffle positioned within the path of the aerosol spray spaced from the spray orifice 42. The aerosol spray impinges upon the surface of the diffuser or baffle, breaking up any large liquid medication droplets that may be entrained in the aerosol spray.

The diffuser assembly 60 can be integrally molded with the cap component. A frusto conical portion 60 can be integrally molded with the cap portion and can extend from the outlet toward the spray assembly. Attached to the frusto conical portion 62 can be legs 64 which extend to a support plate 66. The support plate supports an integrally molded diffuser 68 which extends toward and in proximity to and spaced from the spray orifice 42. The diffuser 68 can have any shape or configuration upon which the aerosol can be impinged. For example, the diffuser can be a flat diffuser or can have a projecting nose portion. When such a projecting diffuser is stabilized, it is preferred to use a generally hemispherical diffuser having a nose portion which is axially aligned with the spray and gas orifices. A preferred diffuser arrangement is shown in FIG. 1 wherein a hemispherically shaped diffuser is axially aligned along axis 70 with the spray and gas orifices.

In operation, the reservoir 14 of the nebulizer 10 can be filled up to a level below the top of the spray nozzle 42 with a liquid medication. A suitable source of compressed gas is connected in flow communication with the gas inlet passage 19 by a suitable conduit attached to the gas inlet 18. The outer end of the aerosol outlet 16 is connected in flow communication to a mask which is to be positioned on a patient.

When the gas source is activated, the gas flows through the gas inlet passage 19, through the gas nozzle 30 and through the gas orifice 32. As the gas exits through the gas orifice, it creates a reduced pressure in the space between the spray and gas orifices. This partial pressure draws the liquid medication through the annular passage 44. The liquid medication seeks its own level within the annular passage 44 prior to activation of the gas source. The partial pressure causes the liquid in the annular passage 44 to flow along that passage to the mixing passage 46 and over the gas nozzle 32. When the stream of gas strikes the liquid medication, it entrains some of such liquid medication in droplet form and carries it along upwardly through the spray orifice 42. As the gas with the entrained liquid passes through the spray orifice, it is dispersed into an aerosol and the aerosol spray continues upward, striking the diffuser 68. When the aerosol spray strikes the diffuser, oversize droplets of liquid medication within the aerosol spray are removed. The oversize droplets removed eventually migrate back to the reservoir 14 and liquid medication in the reservoir.

The aerosol spray continues upwardly around the diffuser and through the aerosol outlet 16 and then on into the patient's respiratory tract.

The liquid medication in the reservoir 14 can continue to seek its own level within the reservoir and the annular passage 44 as the liquid in the reservoir is in fluid flow communication with the annular passage through the liquid passage 52 and space 54 through the sidewall of the spray nozzle. When the nebulizer is maintained in an upright position (axis 70 being vertical), the liquid medication can continually flow into the annular passage 44 through the access provided by the liquid passage 52. When the nebulizer is placed out of such a vertical orientation, such as leaning the nebulizer toward the extended side 48, the liquid medication can continue to flow from the reservoir into the annular passage 44 through the liquid passage 52. Even when the nebulizer is placed in a horizontal position (axis 70 horizontal), the liquid medication will flow toward the sidewall of the nebulizer reservoir, seeking the lowest possible level. As can be seen in the accompanying drawings, the liquid passage 52 can be positioned to extend to such a lowest level for maintaining the liquid medication in communication with the annular passage 44. The liquid passage 52 is spaced from the sidewall 12 and configures to the configuration of the sidewall such that a flow communication is maintained due to the reduced pressure created by the gas flow and the surface tension in the liquid flowing through the liquid passage 52 which maintains a liquid seal along such liquid passage. The upper portion of the extended side 48 extends to the sidewall, providing an interference fit with such an upper portion of the extended side and the sidewall. Air within the housing of the nebulizer does not enter the annular passage 44 when the nebulizer is placed in such a horizontal mode due to the close fitting, preferably interference fitting, of the annular ring 28 extending about the spray nozzle and due to the limited access to the annular passage 44 being through the opening or space 54 which is within the liquid passage 52. In a preferred working embodiment, the annular ring had an inside diameter of about 0.440 inch and a gap of 0.150 inch. The spray nozzle had an outside diameter of 0.435 inch and inside diameter of 0.306 inch. The extended side had a width of 0.125 inch.

The invention herein provides an improvement in the design of nebulizers which includes the ability of the nebulizer herein to use substantially all of the liquid medication introduced to the nebulizer and the ability to provide an aerosol when the nebulizer is placed in a variety of orientations. As can be seen from the drawings and understood from the above discussion, the liquid medication has continual access to the annular passage 44, even when the liquid medication level is extremely low. Thus, a substantial volume of the liquid medication is completely used when a nebulizer of this invention is utilized in patient treatment. In addition, the nebulizer herein can be oriented to fit a particular area or space requirement and still be able to provide a beneficial aerosol spray. The nebulizer herein can be oriented through a 90° angulation and still provide a beneficial aerosol for a patient.

Although the invention of a nebulizer herein has been described in regard to a preferred embodiment, it is not meant to to be limited to such embodiment only as the improved liquid passage assembly can have utility in many nebulizers, including fly-spray types, concentric spray and gas orifice types, and other aligned and nonaligned gas and liquid orifice types of nebulizers.

It is claimed:

1. A nebulizer for converting liquid into aerosol comprising:
   a housing having a liquid reservoir formed by a sidewall of the housing and an outlet opening through which aerosol passes;
   a cylindrical spray nozzle within the reservoir having an end wall defining a spray orofice and having a liquid inlet means in communication with the reservoir for introducing liquid inlet means includes an outwardly extending arm attached to the spray nozzle providing liquid passage means for drawing liquid in the reservoir into the liquid inlet means, which liquid passage means is open to the reservoir and extends conformingly, openly along and spaced from at least a portion of the sidewall of the housing;
   a cylindrical gas nozzle attached to the housing and positioned within the spray nozzle having gas inlet means for introducing gas and an end wall defining a gas orifice, which gas orifice is spaced from and coaxial with the spray orifice, the spray nozzle and gas nozzle defining a liquid passage therebetween extending from the liquid inlet means to the space between the spray and gas orifices; and
   means for preventing the aspiration of air through the liquid passage between the spray nozzle and gas nozzle when liquid is present in the nebulizer reservoir and the nebulizer is oriented in either a vertical position or a horizontal position with the liquid passage means extending radially downwardly, said means for preventing aspiration comprising an annular ring on the sidewall in the reservoir extending circumferentially around the cylindrical spray nozzle and providing a fluid seal between the annular ring and the cylindrical spray nozzle for preventing air from flowing between the annular ring and cylindrical spray nozzle, which annular ring includes a gap which provides a liquid port between the liquid passage means and the liquid passage positioned between the cylindrical spray nozzle and cylindrical gas nozzle.

2. A nebulizer as recited in claim 1 wherein the liquid passage means is open along its length to the reservoir and spaced from the sidewall a distance sufficient for permitting liquid in the reservoir to flow into the liquid passage means and maintain liquid contact between the sidewall and liquid passage means due to surface tension of the liquid.

3. A nebulizer as recited in claim 1 wherein the liquid passage means extends along the portion of the sidewall to a location which would be the lowest location in the reservoir when the nebulizer is positioned such that the portion of the sidewall along which the liquid passage means extends is positioned downward and when an axis extending through the cylindrical gas nozzle and outlet opening is substantially horizontal.

4. A nebulizer as recited in claim 1 wherein the liquid passage means comprises a semicircular channel extending along and spaced from about 0.0010 to about 0.025 inch from the sidewall.

5. A nebulizer as recited in claim 4 wherein the semicircular channel has a radius of about 0.50 inch.

6. A nebulizer as recited in claim 1 wherein the liquid passage means comprises a semicircular channel extending along the outwardly extended arm and which extends along and spaced from about 0.0010 to about 0.025 inch from the sidewall.

7. A nebulizer for converting liquid into an aerosol comprising:
   a housing having a liquid reservoir formed by a sidewall of the housing and an outlet opening through which aerosol passes;
   a cylindrical gas nozzle extending through the reservoir having gas inlet means for introducing gas to the gas nozzle and and end wall defining a gas orifice;
   a cylindrical spray nozzle enclosing the gas nozzle and having an end wall defining a spray orifice, which spray orifice is spaced from and coaxial with the gas orifice, the spray nozzle and gas nozzle defining a liquid annular passage therebetween, which extends to the space between the gas and spray orifices;
   an extended side arm on the spray nozzle which extends radially toward the sidewall of the housing;
   a liquid passage means on the extended side arm which is open along its length and in communication with the reservoir and the liquid annular passage for introducing liquid from the reservoir to the liquid annular passage, the liquid passage means extending conformingly along and spaced from at least a portion of the sidewall of the housing; and
   sealing means for preventing the aspiration of air through the liquid annular passage between the cylindrical spray nozzle and cylindrical gas nozzle when liquid is present in the reservoir and when the nebulizer is oriented in either a vertical position or a horizontal position with the liquid passage means and extended side arm extending radially downwardly, said sealing means for preventing aspiration of air comprising an annular ring on the sidewall in the reservoir extending circumferentially around the cylindrical spray nozzle and providing a fluid seal between the annular ring and the cylindrical spray nozzle for preventing air from flowing between the annular ring and cylindrical spray nozzle, which annular ring includes a gap which provides a liquid port between the liquid passage means and the liquid annular passage.

8. A nebulizer as recited in claim 7 wherein the liquid passage means is spaced from the sidewall a distance sufficient for permitting liquid in the reservoir to flow into the liquid passage means and maintain liquid contact between the sidewall and liquid passage means due to surface tension of the liquid.

9. A nebulizer as recited in claim 7 wherein the liquid passage means is spaced from about 0.0010 inch to about 0.025 inch from the sidewall.

10. A nebulizer as recited in claim 7 wherein the liquid passage means extends along and spaced from that portion of the sidewall of the housing which defines the reservoir.

11. A nebulizer as recited in claim 7 wherein the liquid passage means extends along and spaced from the sidewall up to a location formed by the intersection of the sidewall and a plane formed by radially extending the end wall of the spray nozzle.

12. A nebulizer as recited in claim 7 further comprising a diffuser within the reservoir and supported by attachment to the housing, which diffuser is spaced from the spray orifice.

13. A nebulizer as recited in claim 12 wherein the diffuser comprises a diffuser having a hemispherically-shaped surface wherein the position on the surface of the diffuser closest to the spray nozzle is spaced from and coaxially aligned with the spray nozzle.

14. A nebulizer for converting liquid into an aerosol comprising:
   a housing having a liquid reservoir formed by a sidewall of the housing and an outlet opening through which aerosol passes;
   a cylindrical gas nozzle extending through the reservoir having gas inlet means for introducing gas to the gas nozzle and an end wall defining a gas orifice;
   a cylindrical spray nozzle enclosing the gas nozzle and having an end wall defining a spray orifice, which spray orifice is spaced from and coaxial with the gas orifice, the spray nozzle and gas nozzle defining a liquid annular passage therebetween, which extends to a space between the gas and spray orifices;
   an annular ring on the sidewall extending around the cylindrical spray nozzle and providing a fluid seal between the annular ring and the spray nozzle for preventing the passage of air between the annular ring and cylindrical spray nozzle, which annular ring includes a gap providing a liquid inlet from the reservoir to the liquid annular passage between the cylindrical spray nozzle and cylindrical gas nozzle;
   an extended side arm on the spray nozzle which extends radially to the sidewall of the housing;
   a liquid passage means on the extended side arm in communication with the reservoir and the liquid annular passage through the liquid inlet for introducing liquid from the reservoir to the liquid annular passage, the liquid passage means open along its length to the reservoir and extending conformingly along and spaced from at least a portion of the sidewall of the housing; and
   a diffuser mounted within the housing spaced from the spray orifice, which diffuser has a generally hemispherically-shaped surface wherein the position on the surface of the diffuser closest to the spray nozzle is spaced from and coaxially aligned with the spray nozzle.

* * * * *

UNITED STATES PATENT AND TRADEMARK OFFICE
CERTIFICATE OF CORRECTION

PATENT NO. : 4,566,452

DATED : January 28, 1986

INVENTOR(S) : James I. Farr, deceased, by May S. Farr, administrator

It is certified that error appears in the above-identified patent and that said Letters Patent are hereby corrected as shown below:

Column 7, line 23, change "orofice" to -- orifice --.

Column 7, line 25, after "liquid" insert -- in the reservoir to the spray nozzle, which liquid --.

Signed and Sealed this

Thirteenth Day of May 1986

[SEAL]

Attest:

*Attesting Officer*

DONALD J. QUIGG

*Commissioner of Patents and Trademarks*